United States Patent [19]
Sabsabi et al.

[11] Patent Number: 5,781,289
[45] Date of Patent: Jul. 14, 1998

[54] METHOD AND APPARATUS FOR RAPID IN SITU ANALYSIS OF PRESELECTED COMPONENTS OF HOMOGENEOUS SOLID COMPOSITIONS, ESPECIALLY PHARMACEUTICAL COMPOSITIONS

[76] Inventors: Mohamad Sabsabi, 453 Darontal, #417, Boucherville, Québec, Canada, J4B 6J4; Jean F. Bussiere, 1000 Des Tilleuls, #4, St. Bruno, Québec, Canada, J3V 5N8

[21] Appl. No.: 744,213

[22] Filed: Nov. 5, 1996

[51] Int. Cl.$^6$ .................................................. G01N 21/63
[52] U.S. Cl. .................................................. 356/318
[58] Field of Search .................................. 356/317, 318

[56] References Cited

U.S. PATENT DOCUMENTS

| 4,645,342 | 2/1987 | Tanimoto et al. | 356/318 |
| 5,504,332 | 4/1996 | Richmond et al. | 250/339.11 |

FOREIGN PATENT DOCUMENTS 4004627 2/1991 Germany.

OTHER PUBLICATIONS

M. Sabsabi et al. Appl. Spectroscopy, 49, 499, 1995.
M. Sabsabi et al. XXII ICPIG Proc., New Jersey, Aug., 1995.

*Primary Examiner*—F. L. Evans
*Attorney, Agent, or Firm*—Juliusz Szereszewski

[57] ABSTRACT

A method and apparatus for rapid in-situ spectroscopic analysis of preselected components of homogeneous solid chemical compositions, especially pharmaceutical products. The apparatus comprises a high-power pulsed laser whose beam is focused on the material, typically a tablet or the powder prior to compaction into the tablet, which generally consists of an active ingredient (e.g. a drug) and a filler material (cellulose, glucose, lactose, etc.). The pulsed laser beam vaporizes a small volume of the pharmaceutical product and produces a plasma having an elemental composition which is representative of the pharmaceutical product. The atomic composition of the vaporized material is analyzed with an optical spectrometer. As the temperature of the plasma is sufficiently elevated to cause dissociation of the molecules of the constituents of the pharmaceutical product, the concentration of the active ingredient is obtained by analyzing the atomic concentration of an element which is present in the active ingredient but not in the matrix or filler material, or whose concentration in the active ingredient is substantially different from the matrix, and acts as a tag on the active material. The technique can also be used to analyze inactive ingredients or the presence of unwanted contaminants which consist of elements not normally present in such pharmaceutical products such as trace metals introduced accidentally during processing.

5 Claims, 4 Drawing Sheets

METHOD AND APPARATUS FOR RAPID IN SITU ANALYSIS OF PRESELECTED COMPONENTS OF HOMOGENEOUS SOLID COMPOSITIONS, ESPECIALLY PHARMACEUTICAL COMPOSITIONS

BACKGROUND OF THE INVENTION

1. Field of the Invention

This invention relates to a spectroscopic method and apparatus for analysis of substantially homogeneous chemical compositions or products, particularly pharmaceutical compositions, to determine the concentration of an active or inactive ingredient, or the presence and concentration of unwanted elements, such as trace metals, in such compositions or products.

2. Related Art

The pharmaceutical industry strives to ensure the purity and efficacy of its products. Bound by regulations, the industry must fully characterize drug substances prior to consumer use. While much emphasis is on the organic moieties, trace metal concentrations in drugs are increasingly important. Drug purity, catalyst and metallic residues from processing equipment, cleaning validations, homogeneity and control of the pharmaceutical active agent in tablets are all of concern.

The pharmaceutically active agent whose quantity must be on target within known accuracy, often constitutes only a small fraction, typically 5%, of the tablet mass. The majority of the tablet mass is usually composed of cellulose, lactose and a binding element (magnesium stearate), inert materials used to facilitate tablet compaction and drug absorption by the patient. Control of the active agent is usually done off line, so that a substantial time lag may exist between the beginning of the procedural problem and its recognition.

Drug analysis is one of the most painstaking tasks for the analytical spectroscopist. Most modern techniques, whether based on atomic spectroscopy or liquid chromatography, require that the sample be dissolved. This dissolution step increases the cost and time of analysis; it also increases the likelihood of contamination and of inaccurate results.

Liquid chromatography is generally considered the most sensitive technique for drug analysis. It involves the separation of a mixture into its components by introducing it into a liquid mobile phase which passes through a stationary phase consisting of solid particles, usually packed in a column. Different components of the mixture interact with the phases in different ways. Depending on the relative strengths of the interactions between the solid phase and the mobile phase, certain components of the mixture will take longer to pass through the stationary phase than others. Once a separation is effected, the various components can be detected and quantitatively measured. Most liquid chromatography performed today is done using high pressure to speed up the analysis and is known as HPLC, or high performance liquid chromatography. For a drug analysis by this technique, the sample must be in a solution. Dissolving the active agent is often a difficult task and may require extensive sample preparation and lengthy extraction in an organic solvent. This sample preparation step increases the probability for sample contamination. Depending on the nature of the active agent and its dissolution, the analysis time is in the range of one hour which makes this technique inefficient for on line analysis of drugs.

In inductively coupled plasma optical emission spectroscopy (ICP-OES), the material to be analyzed is prepared as an aerosol which is injected with an argon gas flow into an inductively heated plasma torch. In the central part of this stationary plasma exist temperatures in the range of 6000 to 8000K. At these temperatures, the aerosols are effectively atomized and in excited states. The optical emission is then observed with a polychromator to perform multi-element analysis. ICP method has been used for trace elements of heavy metals such as mercury, lead or tin in drug solutions. The analysis by this technique requires that the sample must be dissolved. As explained above, the dissolution of the sample makes this technique not useful for rapid analysis and eliminates the possibility of using it for on-line measurement.

Graphite furnace atomic absorption spectroscopy (GF-AAS) utilizes the specific absorption features of elements. The substance to be analyzed is dissolved and a droplet of the obtained solution is fed into a graphite furnace. The electrically heated furnace atomizes the droplet to form a cloud of atoms. The absorption of the radiation from an element specific lamp along the axis of the furnace is observed to determine the concentration of this element.

The conventional techniques mentioned above are predominantly used in laboratories which are separated from the production line. Moreover, they are also labor intensive because of the long time required for sample preparation and analysis.

U.S. Pat. No. 4,986,658 to Kim describes a probe for molten metal analysis. The probe contains a high-pulsed laser producing a pulsed laser beam having a triangular pulse waveshape. When the probe is immersed in the molten metal, the pulsed laser beam vaporizes a portion of the molten metal to produce a plasma having an elemental composition representative of the molten metal composition. Within the probe, there is provided a pair of spectrographs each having a diffraction grating coupled to a gated intensified photodiode array. The spectroscopic atomic emission of the plasma is analyzed and detected for two separated time windows during the life of the plasma using two spectrometers in parallel. The gate windows are in the first 50–200 ns period and 1 to 5 μs after the laser pulse.

Buchel et al. German Patent No. DE 40 04 627 A1 describe a device based on laser induced plasma spectroscopy for the determination of material homogeneity of polymeric materials such as plastics and rubber, based on concentration distribution measurements of elements during manufacturing or finishing. The Buchel et al technique makes it possible to make statements about the degree of global homogeneity (degree of mixing) and the degree of dispersion of selected material constituents. On the basis of the information obtained from several measuring points, checked successively, a concentration value curve can be obtained of selected elements. Buchel et al. deal with polymeric materials and uses molecular bands.

U.S. Pat. No. 5,379,103 to Zigler describes a mobile laboratory for in situ detection of organic and heavy metal pollutants in ground water. Pulsed laser energy is delivered via fiber optic media to create a laser spark on a remotely located analysis sample. The system operates in two modes: one is based on laser induced plasma spectroscopy and the other on laser induced fluorescence. In the first operational mode, the laser beam guided by optical fiber is focused by a lens on the sample to generate a plasma. The emitted spectrum is analyzed and used to detect heavy metals. In the second mode the focusing laser energy is removed allowing the laser beam via fiber optic to irradiate the sample, so that organic molecules with an aromatic structure emit absorbed ultraviolet energy as fluorescence. The emitted fluorescence light is transmitted via fiber optic media for further analysis. The measured wavelength and time characteristics of the emitted fluorescence can be compared against predetermined characteristics to identify the organic substances in the analysis sample. Zigler et al analyze trace quantities of both molecules and atoms in ground water. In the case of molecules, molecular spectra are analyzed using fluorescence.

SUMMARY OF THE INVENTION

As explained above, laser induced plasma spectroscopy has been used in various scientific and industrial applications, and in particular, in materials processing, environment fields and molten metals. However, laser induced plasma spectroscopy has not been used for the analysis of drugs and no mention is made of the tagging of active agent by atomic specified element of the instant invention. Furthermore, all existing techniques for measuring the percentage of active ingredient are based on molecular structure and not on tagging with a specific atom or atoms.

In industrial pharmaceutical processes, there is a great need for on-line and off-line control of the concentration of active agent in tablets and the on-line blend uniformity of the different ingredients in mixers and hoppers.

Accordingly, it is an object of this invention to provide a new method and apparatus for in situ transient spectroscopic analysis of solid compositions having a molecular component dispersed throughout the composition, e.g. pharmaceutical products such as powders and tablets, which is free of the problems of the prior art and which provides an accurate and reproducible indication of the concentration of the component, e.g. active ingredient (drug) in the pharmaceutical product during a short time, in the order of seconds.

It is a further object of this invention to provide a novel method and apparatus, as above noted, by which concentration of undesirable trace elements in such compositions as defined above can be rapidly obtained.

These and other objects are achieved according to the invention by providing a method and apparatus for in situ measuring the content of a predetermined molecular component of a solid chemical composition which comprises the component dispersed substantially homogeneously within a matrix, the method comprising:

emitting laser pulses from a laser energy emitter, focusing said pulses on a sample of said solid composition to generate a plasma containing elemental radiation derived from separate chemical elements of said molecular component measuring the radiation intensity of a wavelength of the radiation which is representative of a preselected chemical element which is present in said molecular component at a different concentration than in the matrix of said composition, and determining the content of said predetermined component in said composition as a function of said radiation intensity.

Preferably, the preselected chemical element is such as to be absent from the matrix. Generally, however, the method of the invention is feasible where the difference in concentration between the molecular component and the matrix is substantial.

The radiation intensity representative of the selected chemical component, or tag, is measured in a time-dependent manner to optimize the spectrochemical analysis.

In another aspect of the invention, there is provided an apparatus for measuring the content (quantitative analysis) of a molecular component of a solid chemical composition which comprises said component dispersed substantially uniformly throughout a matrix, the apparatus comprising a laser energy emitter, means for focusing energy emitted from said laser emitter on a sample of said solid composition, thereby generating a plasma containing elemental radiation derived from separate chemical elements of said molecular component, means for spectrally and temporally analyzing the intensity of the elemental radiation which is characteristic of a preselected chemical element that is present in the molecular component at a different concentration than in the matrix of said composition.

Further, the apparatus comprises delay means for gating off a phase in plasma development wherein atomic spectra of said molecular element are insufficiently pronounced.

The active agent in the tablet can be tagged by certain elements such as phosphorus, sodium, sulfur, or other elements, which are not present in the inactive filler (typically lactose, cellulose, etc.) constituting the drug matrix and which are detected in proxy to the actual detection of lines characteristic of the molecular structure of the active ingredient. In other words, instead of detecting the molecular spectrum of the active ingredient, the line of the atomic tracer element is measured and ratioed to a reference carbon line.

Laser-focusing provides excellent spatial resolution, allowing the study of the spatial homogeneity of active drug components or trace elements on the surface or in the bulk of pharmaceutical products

BRIEF DESCRIPTION OF THE DRAWINGS

The invention will be described in more detail in the following description to be taken in conjunction with the drawings in which.

DETAILED DESCRIPTION OF THE PREFERRED EMBODIMENTS

Figure 1:
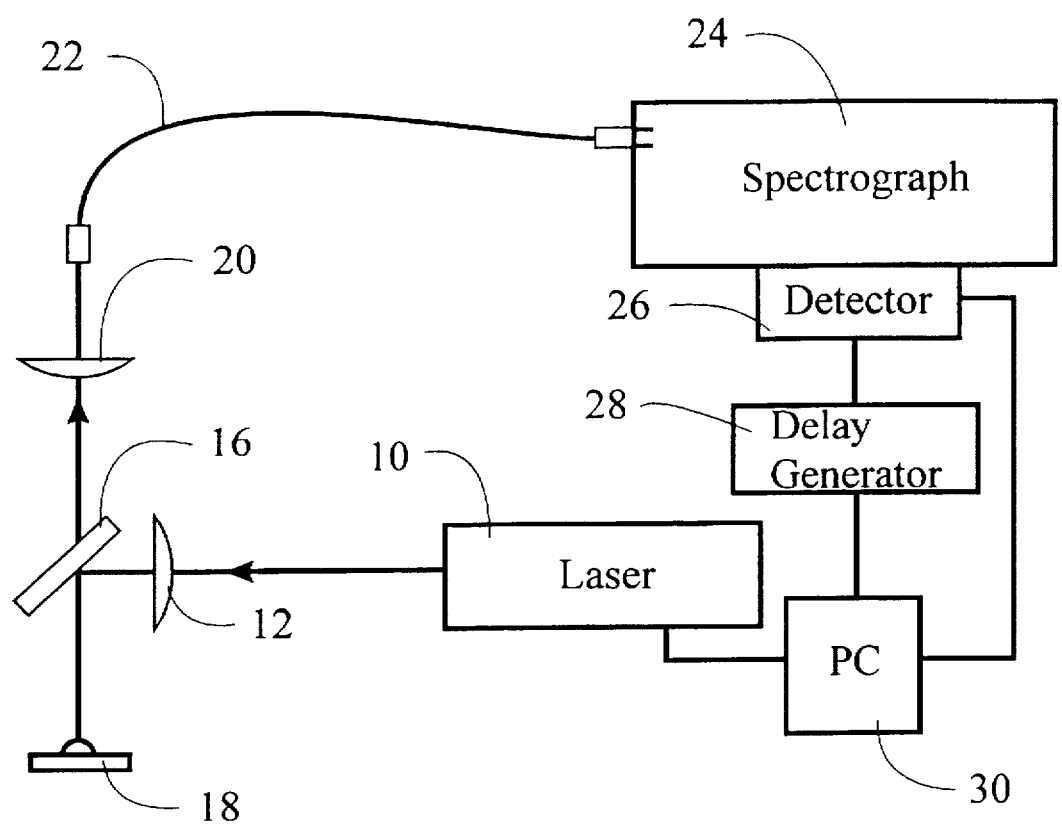
FIG. 1 is an overall block diagram of the apparatus of the invention.

The method and apparatus of the invention use powerful laser pulses to irradiate a representative quantity of drug sample and form a microplasma or spark on a sample. As a result of the high temperature plasma generated, a small amount of the material is vaporized and ionized, molecules are dissociated, and atoms and ions are in excited states, thus allowing emitting species in th e plasma to be identified by spectrally and temporally resolving the spark light FIG. 1 shows a schematic diagram of the apparatus of the invention. A Nd:YAG laser 10 is disposed so as to deliver energy pulses through a lens 12, an optional optical fiber and a dichroic mirror 16 to a sample 18 to generate a plasma. The light emitted by the plasma is collected by an optical system consisting of a lens 20 and an optical fiber 22, to the entrance of an optical spectrometer 24 where it is detected in the focal plane by means of an optical multichannel analyzer with high time resolution (on the microsecond scale). Time resolution of the emitted light is used to reduce interferences and background.

The spectrometer is equipped with a diffraction grating coupled to a gated, intensified photodiode array detector 26 or other means to detect simultaneously and during a specified time, the specific-element line for several elements found in the molecular component of the sample. A delay generator 28 is installed in the system for gating off the early stage of plasma formation as described hereinbelow. A fast computer 30 evaluates the measured spectra and calculates the element concentrations via calibration procedures.

Three phases can be distinguished in the transient plasma lifetime depending on the nature of the plasma.

At the time of the initial breakdown and during the pulse, the plasma becomes an electron-rich environment. The initially transparent matter present in the focal volume becomes optically opaque, absorbing the laser beam. The plasma is characterized by high electron density and temperature. The lines are very broad and the continuum is very strong.

At the end of the laser pulse, temperature and electron density drop very quickly during this period from their maximum reached by the end of the laser pulse. Recombination and de-excitation events begin to prevail and the breakdown material returns to ground state atomic and molecular species. The kinetics during this intermediate time can be described as a state of quasi equilibrium and there are relatively small temperature changes observed over a microsecond timescale (see M. Sabsabi et P. Cielo, AppL. Spectrosc., 49, 499, 1995).

During the last final stage in the plasma lifetime, the contents of the plasma volume and its local pressure return to ambient conditions (See M. Sabsabi et al XXII ICPIG Proc., New Jersey, August 1995). Under these conditions, the ambient buffer gas goes into the plasma volume. This increases the plasma inhomogeneity and decreases reproducibility, stability and signal to noise ratio.

The second phase of the plasma lifetime is favorable for spectrochemical analysis according to the invention. By gating off the earlier part of the plasma, one can improve the signal to noise ratio, the lines are narrow and well resolved.

Figure 2A:
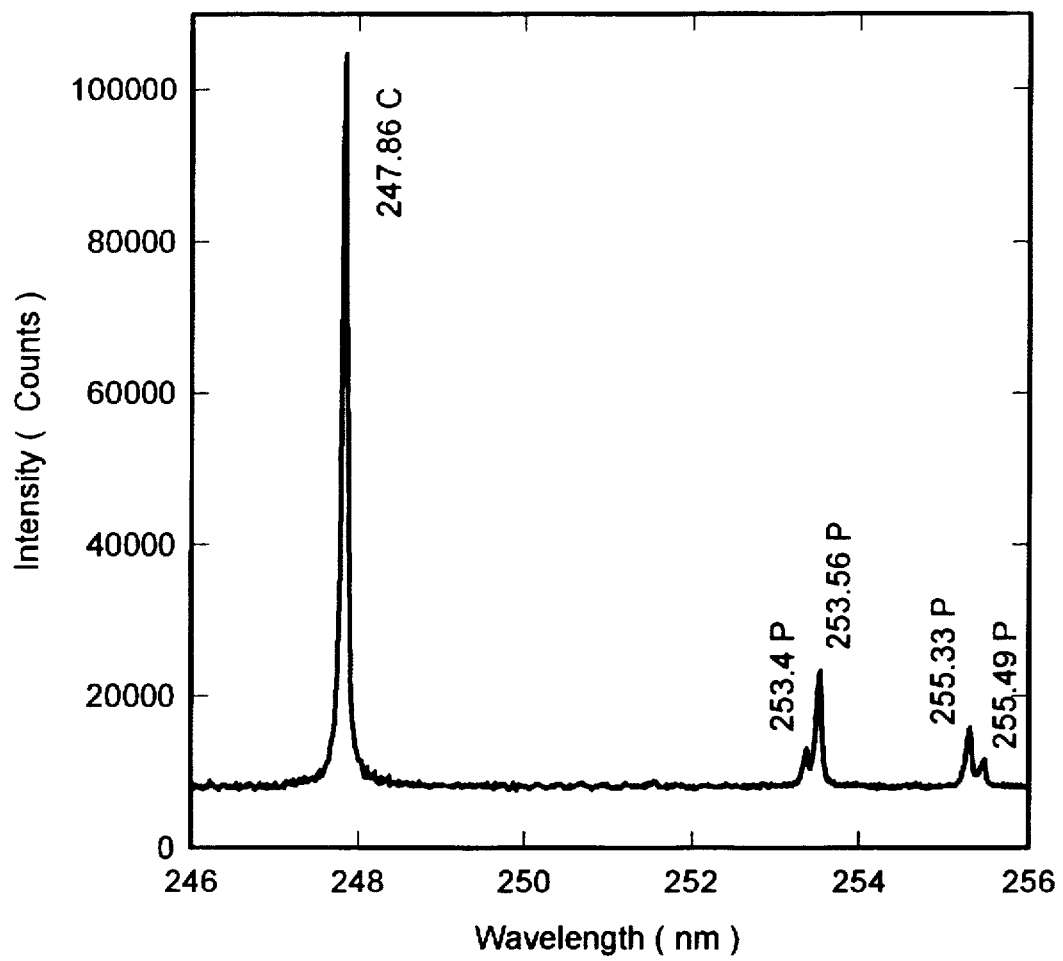
FIG. 2a shows an optical spectrum emission obtained with a Nd-YAG Q-switched laser, of a pharmaceutical product with an active ingredient containing phosphorus as the tag element.

An exemplary spectrum obtained in the actual experiments is shown in FIG. 2a. It is produced by gating off an early phase of plasma development, as explained herein.

Figure 2B:
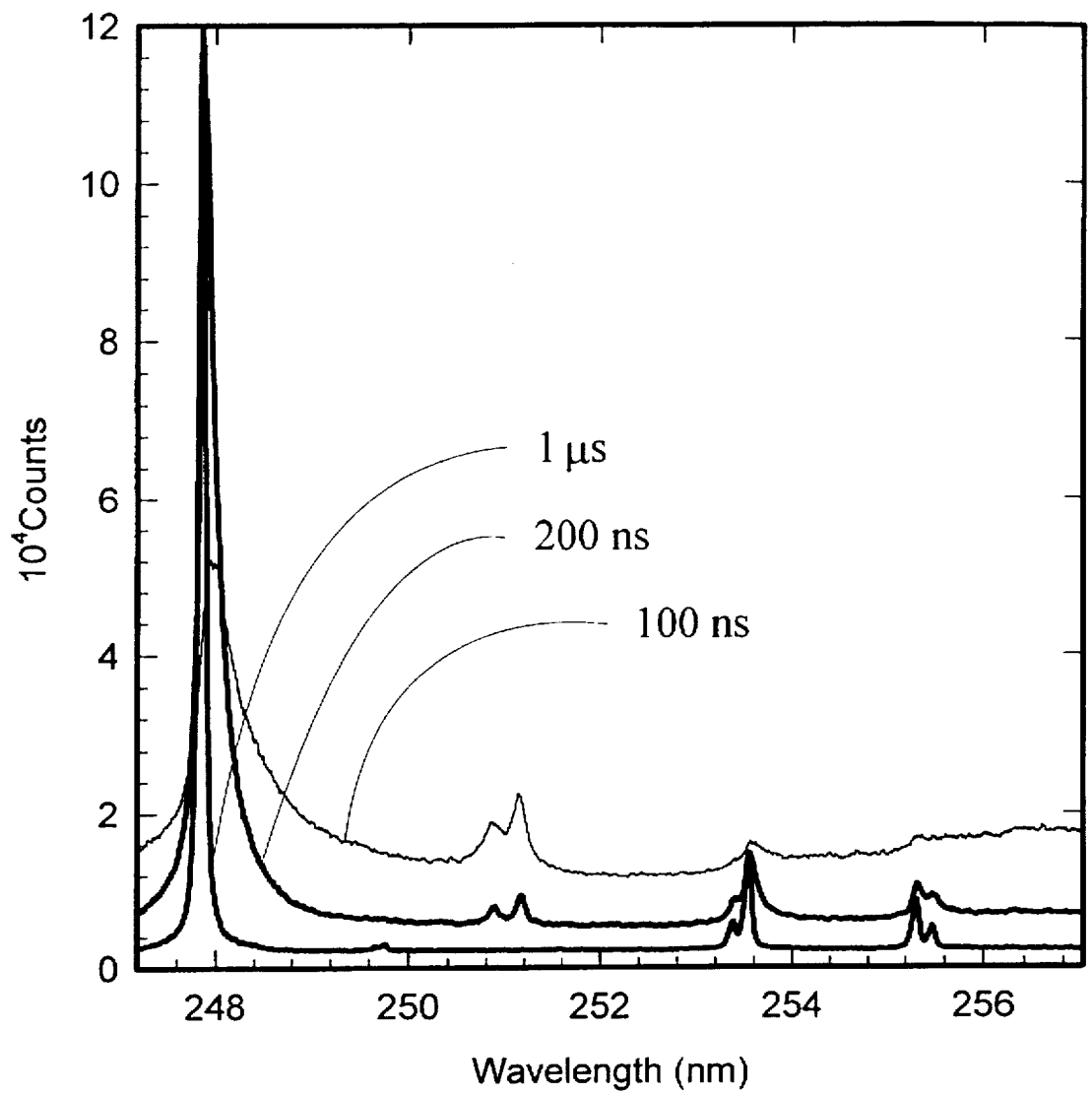
FIG. 2b shows a time-resolved spectrum analogous to that of FIG. 2a to illustrate the importance of time-delay.

As shown in FIG. 2b, immediately after the laser pulse the plasma emission consists of an intense continuum and emitted light consists initially of very broad lines due to high electron density (lines at 100 and 200 ns). Typically, 1 μs after the laser pulse, the Stark effect is decreased significantly, the lines are narrower and well resolved, and the signal-to-noise ratio is improved. Under these conditions, the atomization is complete and the plasma is close to local thermal equilibrium and is favorable for spectrochemical analysis. This avoids the non linear phenomena and improves the accuracy of the measurement.

The optimum delay time should be determined experimentally for each compound analyzed. The delay time depends on the target compound, the laser energy, the ambient gas and its pressure.

The radiation emitted by the laser induced plasma is therefore collected at a time delay preferentially of 1 μs after the laser pulse and during 3 μs time period using an optical gating system. During that time, all emission lines become narrow, better defined and well resolved. In addition, the plasma is optically thin for most of non resonant lines, a favorable condition for quantitative analysis. The optimum duration window depends on the laser parameters, the nature of the buffer gas and the tracer elements.

The spectroscopic analysis employed in the instant invention can be termed Laser Induced Plasma Spectroscopy (LIPS).

In tests conducted to validate the invention, a pharmaceutical composition alendronate sodium (generic name bis-phosphonate, commercial name FOSAMAX) was used as the active compound. The concentrations of phosphorus and the active compound in the tablets are indicated in Table 1. The tablet matrix was formed mainly by carbon (approximately 90%), oxygen, nitrogen, and magnesium stearate. The laser used was a Nd:YAG laser capable of delivering 250 mJ in 7 ns at a rate of 10 pulses by second and operating at 1064 nm.

The laser need not be a high energy laser, but must generate high peak power that can be focused to about $2.10^9$ W/cm$^2$. Another possible choice is a $CO_2$ laser or an excimer laser. The pulses are focused on the tablet by a lens to produce rapid vaporization, dissociation of the active agent and excitation of atomic levels by generating a plasma with high temperature.

The spectrometer was a McPherson spectrograph with 0.67 m focal length and 2,400 grooves per mm.

The plasma generated produces a radiation which is characteristic of the elements contained in the sample and which is supplied to the spectrometer. In the latter, the plasma radiation is dispersed into a spectrum by means of grating and recorded, time-delayed, by diode line type detector in the form of individual spectral lines. Alternately, one can use an array of photomultipliers or other suitable detectors. After release of a laser beam, the detector unit, after a time delay of 1 μs, is illuminated for at least 3 μs. The digitized spectrum is then passed to the computer for storage and analysis.

To be suitable for active agent determination in pharmaceutical compositions, the plasma must be representative of the composition of the sample and the parameters affecting the plasma must be controlled.

Both the active agent and the matrix generally consist of powders which are mixed with the aim of producing an homogeneous blend which can then be compressed into individual tablets having a uniform concentration of the active ingredient. As the drug and matrix particle size varies generally from 10 to 20 mm, it is necessary to sample a volume which encompasses a large number of particles to avoid inaccuracies associated with sampling which is performed on too small a spatial scale. Thus to assure that the plasma plume has a composition representative of the drug concentration in a tablet, the Q-switched laser of the present invention is directed at the surface of the tablet with a focus spot having an area of 1–4 mm$^2$, at the stated power density of $\sim 2 \cdot 10^9$ W/cm$^2$. For example, these conditions could be fulfilled by a 6 ns Nd-YAG laser pulse, having 250 mJ energy, focused on the sample with a 2 mm diameter spot. The spot size is large enough to minimize the influence of the sample's spatial inhomogeneity while having enough energy density to populate the excited levels of the preselected "tracer" element or elements of the active agent in pharmaceutical or other compositions.

The active agent molecule used in the samples shown in Table 1 contains 2 atoms of phosphorus. The analysis by LIPS is based mainly on atomic emission spectroscopy because the atomic spectra are well documented and less complicated than the molecular spectra. Also, the molecular spectrum of the new active agent is generally not known. The measurement of phosphorus concentration allows the determination of active agent concentration.

In the examples, several lines for phosphorus and carbon were identified. To deduce the concentration of active ingredient we have chosen the following atomic lines: P 253.56 nm and C 247.86 nm. FIG. 2 shows a typical spectrum obtained on the 2.5% weight drug in tablet. These lines have similar excited energy levels, so that their intensity ratio is only slightly affected by variations in the plasma temperature. Moreover, they are detected at the same time in the same spectral window, thus avoiding variations in relative intensity from shot to shot. According to Boltzmann law, the ratio P/C is directly related to the concentration ratio of these elements and independent of the laser intensity variations. A calibration curve can thus be obtained for example for the samples mentioned in Table 1, by relating the P/C line intensity ratio to the drug concentration in the sample. The tablet contains more than 90% of carbon, which had sufficiently homogenous distribution for internal standardization. The intensity of the 247.9 nm carbon line was used as reference for internal standardization. Because the carbon matrix spectrum is not very rich compared, for instance to a metallic matrix, the spectrometer does not need high power resolution in these conditions.

For the compound used, alendronate sodium, and the samples described in Table 1, it was possible to relate the P/C line intensity ratio to the drug concentration in the tablets. By relating the experimental values of the P/C line intensity ratio to the drug concentration, one can obtain a calibration curve similar to that of FIG. 3. The mathematical relationship can be e.g. stored in a computer memory. The P/C line intensity ratio of unknown samples can thus be measured to determine the concentrations using the calibration curve.

Figure 3:
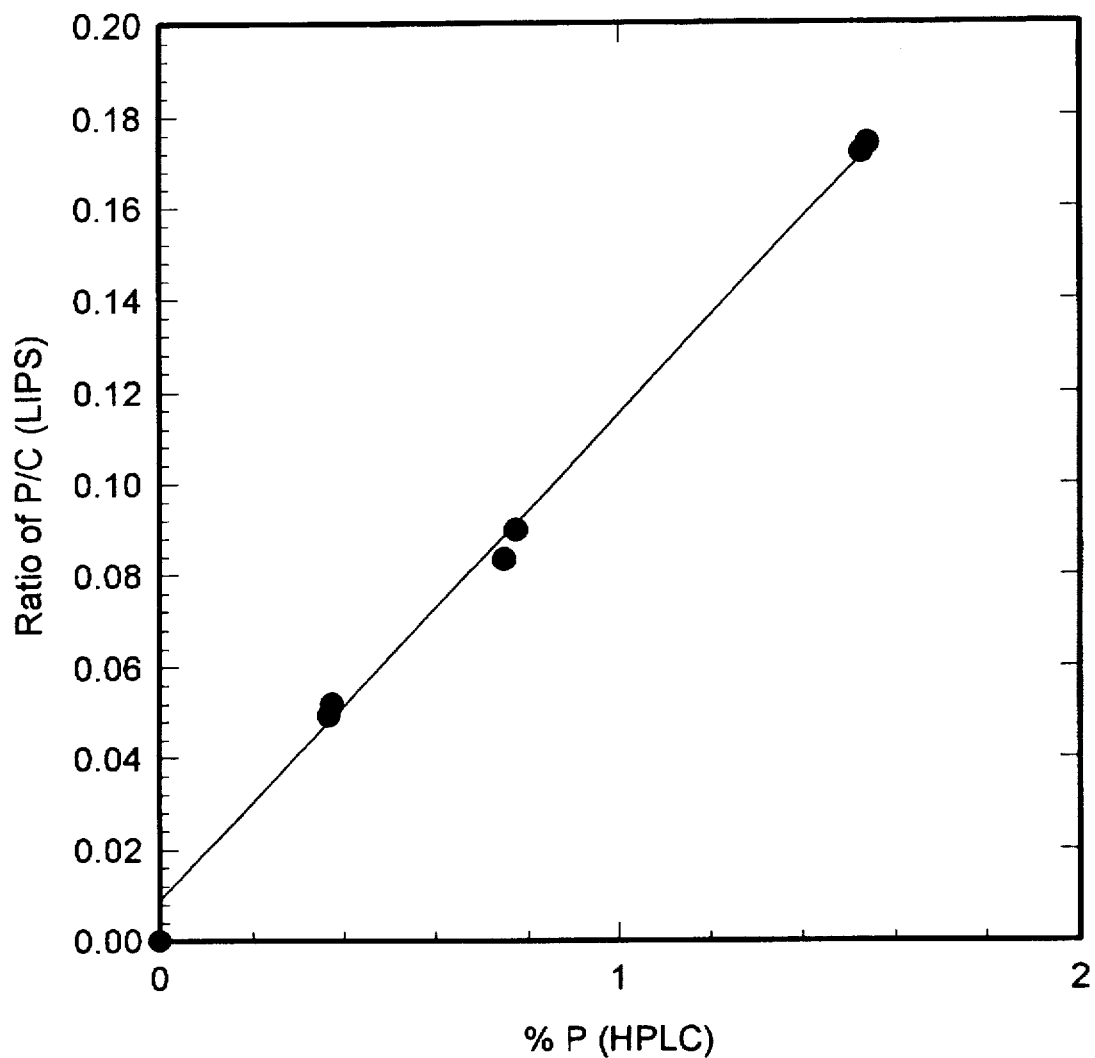
FIG. 3 shows a comparison between the results obtain ed by high performance liquid chromatography and those obtained by laser induced plasma spectroscopy.

There is a good agreement between the values obtained by this invention and those given by HPLC as shown in FIG. 3. The curve is linear for the range of concentrations available in the samples. The maximum deviation between the values given by both techniques is less than the 5% deviation tolerated by the industry for the pharmaceutical active agent in the tablet.

In the pharmaceutical industry, the invention can be used in various ways. One possibility is to sample each tablet; another is to select one tablet for a given number to be analyzed. These approaches depend on the analysis time of the invention which is limited by the laser frequency. It is possible to analyze each tablet by using a 100 Hz YAG laser on the basis of one single shot measurement. This depends on the tolerated deviation of drug concentration and the sampling method as well as requires the surface to be representative of the bulk. In the case of sampling one tablet selected from a given number, we can carry out 1200 measurements with a 20 Hz YAG laser in one minute untervals (i.e. 1200 measurements corresponds to one minute intervals). The spatial element distribution and the concentration of active agent can be measured. In either situation the rejection rate is reduced to a minimum because the results are obtained very fast compared with other known analytical methods. For example, the off-line determination by HPLC requires sample preparation and analysis that takes one hour or more. Thus, the present invention allows to minimize the rejection rate from one-hour to one-minute production.

Alternatively, the spatial distribution of the preselected element can be measured on line in the hopper. The element composition and homogeneity of the drug matrix material can be monitored frequently during the mixing process. In the hopper, one can use a probe, e.g. a tube, through which the laser is focused on the drug.

TABLE I

| | Phosphorus concentration [%] weight in tablet. | | | |
|---|---|---|---|---|
| Tablet sample | Placebo | A | B | C |
| Drug (%) in tablet | 0 | 5% | 2.5% | 1.25% |
| P (%) in tablet | 0 | 1.5% | 0.75% | 0.37% |

P (%) measured by conventional techniques.
All percent values are by weight.

It is an advantage of the invention that the analysis is carried out on a solid phase sample. The interaction of the laser with a liquid is different from the interaction with a solid because the process of melting is absent and the transport properties and optical reflectance vary considerably between the two phases and materials. The experimental conditions for the analysis of molten metal are different from those in the process of the present invention where only one spectrometer is used.

We claim:

1. A method of in-situ measuring the content of a predetermined molecular component of a solid chemical composition, the molecular component being dispersed substantially homogeneously within a matrix, the method comprising:

emitting laser pulses from a laser energy emitter, focusing said pulses on a sample of said solid composition to generate a plasma containing elemental radiation derived from separate chemical elements of said molecular component measuring the radiation intensity of a wavelength of the radiation which is representative of a selected chemical element which is present in said molecular component at a different concentration than in the matrix of said composition, and determining the content of said predetermined component in said composition as a function of said radiation intensity.

2. The method of claim 1 wherein said predetermined component is an active agent of a pharmaceutical composition.

3. The method of claim 1 wherein said content of said component is determined by comparing said radiation intensity with a known radiation intensity of said chemical element.

4. The method of claim 1 wherein for the purpose of said determination, the radiation intensity is measured at a time slot which corresponds to a substantially complete atomization of said plasma.

5. The method of claim 1 wherein said pulses are focused on said sample on a spot of a size sufficient to account for the spatial homogeneity variance of said molecular component through said matrix.

* * * * *